(12) United States Patent
Thompson (10) Patent No.: US 10,825,239 B2
(45) Date of Patent: Nov. 3, 2020

(54) ORTHODONTIC TREATMENT SIMULATION HAVING IMPROVED GRAPHICS PROCESSING FOR VIRTUAL MODELING

(71) Applicant: CLEARCORRECT OPERATING, LLC, Round Rock, TX (US)

(72) Inventor: Lance Thompson, Houston, TX (US)

(73) Assignee: CLEARCORRECT OPERATING, LLC, Round Rock, TX (US)

( * ) Notice: Subject to any disclaimer, the term of this patent is extended or adjusted under 35 U.S.C. 154(b) by 0 days.

(21) Appl. No.: 16/395,297

(22) Filed: Apr. 26, 2019

(65) Prior Publication Data

US 2019/0252057 A1 Aug. 15, 2019

Related U.S. Application Data

(63) Continuation of application No. 15/624,123, filed on Jun. 15, 2017, now Pat. No. 10,331,859.

(Continued)

(51) Int. Cl.
*G06T 17/00* (2006.01)
*A61C 7/00* (2006.01)
(Continued)

(52) U.S. Cl.
CPC .............. *G06T 17/00* (2013.01); *A61C 7/002* (2013.01); *A61C 9/0046* (2013.01); *G06F 19/3481* (2013.01); *G16H 50/50* (2018.01)

(58) Field of Classification Search
CPC ....... G06T 17/00; A61C 7/002; A61C 9/0046; A61C 2007/004; G16H 50/50; G16H 20/40; G06F 19/3481
See application file for complete search history.

(56) References Cited

U.S. PATENT DOCUMENTS 6,089,868 A 7/2000 Jordan et al.
6,514,074 B1 * 2/2003 Chishti ................ A61C 9/0046
433/24

(Continued)

FOREIGN PATENT DOCUMENTS

AU 2017281611 11/2018
BR 112018073993 A2 2/2019
(Continued)

OTHER PUBLICATIONS

Examination Report No. 1 issued in AU Application No. 2017281611 dated Jun. 28, 2019.
(Continued)

*Primary Examiner* — William A Beutel
(74) *Attorney, Agent, or Firm* — Gardella Grace P.A.

(57) ABSTRACT

According to embodiments of the disclosed subject matter, a server can include processing circuitry configured to receive a virtual modeling file encoded with an orthodontic treatment plan such that the encoded information of the virtual modeling file format allows all steps of the orthodontic treatment plan to be displayed without a separate file for each treatment step. Additionally, the processing circuitry can be configured to download a first treatment step of the virtual modeling file format, receive gingiva and teeth geometries corresponding to the first treatment step, and display the first treatment step. Further, a selected treatment step can be displayed based on information encoded into the orthodontic virtual modeling file format.

17 Claims, 6 Drawing Sheets

Related U.S. Application Data (60) Provisional application No. 62/352,844, filed on Jun. 21, 2016.

(51) Int. Cl.
*G16H 50/50* (2018.01)
*A61C 9/00* (2006.01)
*G06F 19/00* (2018.01)

(56) References Cited

U.S. PATENT DOCUMENTS

| | | | |
|---|---|---|---|
| 7,027,642 B2 * | 4/2006 | Rubbert | A61C 7/00 |
| | | | 382/154 |
| 7,361,017 B2 | 4/2008 | Sachdeva et al. | |
| 7,471,821 B2 | 12/2008 | Rubbert et al. | |
| 7,641,473 B2 | 1/2010 | Sporbert et al. | |
| 8,047,847 B2 | 11/2011 | Kaufmann et al. | |
| 8,177,551 B2 | 5/2012 | Sachdeva et al. | |
| 8,740,614 B2 | 6/2014 | Wen et al. | |
| 8,807,999 B2 | 8/2014 | Kuo et al. | |
| 9,161,824 B2 | 10/2015 | Chishti et al. | |
| 10,331,859 B2 | 6/2019 | Thompson | |
| 2001/0002310 A1 * | 5/2001 | Chishti | A61C 7/08 |
| | | | 433/24 |
| 2004/0029068 A1 * | 2/2004 | Sachdeva | A61C 9/0046 |
| | | | 433/24 |
| 2004/0197727 A1 * | 10/2004 | Sachdeva | A61C 13/0004 |
| | | | 433/24 |
| 2005/0240646 A1 | 10/2005 | Lin | |
| 2010/0260405 A1 | 10/2010 | Cinader, Jr. | |
| 2011/0082669 A1 | 4/2011 | Taub et al. | |
| 2011/0268327 A1 | 11/2011 | Getto et al. | |
| 2012/0015316 A1 | 1/2012 | Sachdeva et al. | |
| 2012/0244488 A1 | 9/2012 | Chishti et al. | |
| 2014/0379356 A1 | 12/2014 | Sachdeva et al. | |
| 2015/0305830 A1 | 10/2015 | Howard et al. | |
| 2017/0364662 A1 | 12/2017 | Thompson | |

FOREIGN PATENT DOCUMENTS

| | | | |
|---|---|---|---|
| CA | 3024328 | 12/2017 | |
| CN | 109310485 | 2/2019 | |
| EP | 3471652 A1 | 4/2019 | |
| EP | 3471652 | 8/2020 | |
| JP | 2002514465 | 5/2002 | |
| JP | 2005523795 | 8/2005 | |
| JP | 2011500142 | 1/2011 | |
| JP | 2019518538 | 7/2019 | |
| KR | 20190033523 | 3/2019 | |
| KR | 102137343 | 7/2020 | |
| WO | WO-0180761 A2 * | 11/2001 | A61C 9/0053 |
| WO | 2017223062 | 6/2017 | |

OTHER PUBLICATIONS

Extended European Search Report issued in EP Application No. 17816047.9 dated May 27, 2019.
Sousa et al., "Accuracy and reproducibility of 3-dimensional digital model measurements," American Journal of Orthodontics and Dentofacial Orthopedics, vol. 142, Issue 2, pp. 269-273 (2012).
International Search Report dated Sep. 8, 2017 in International Application No. PCT/US2017/038288.
Written Opinion dated Sep. 8, 2017 in International Application No. PCT/US2017/038288.
Non-Final Office Action issued in U.S. Appl. No. 15/624,123 dated Sep. 19, 2018.
Notice of Allowance issued in U.S. Appl. No. 15/624,123 dated Feb. 19, 2019.
International Preliminary Report dated Dec. 25, 2018 in International Application No. PCT/US2017/038288.
Office Action issued by the Korean Intellectual Property Office ("KIPO") dated Apr. 29, 2020 (English translation provided).
Office Action issued in related Japanese Application No. 2018-562121 on Aug. 4, 2020 (translation included).

* cited by examiner

ORTHODONTIC TREATMENT SIMULATION HAVING IMPROVED GRAPHICS PROCESSING FOR VIRTUAL MODELING

CROSS-REFERENCE TO RELATED APPLICATION

This application is a continuation of U.S. application Ser. No. 15/624,123, filed Jun. 15, 2017, which claims the benefit of U.S. Provisional Application No. 62/352,844, filed Jun. 21, 2016.

BACKGROUND

With the emergence of computer-based, virtual modeling, virtual reality and 3D/4D imaging technology, orthodontists can model patients' teeth in detail to arrive at a treatment plan or diagnosis. For example, an orthodontist can use virtual modeling to display individual treatment steps of a treatment plan, each step stored and rendered in a separate 3D file.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

According to embodiments of the disclosed subject matter, a server can include processing circuitry configured to receive a virtual modeling file encoded with an orthodontic treatment plan such that the encoded information of the virtual model file format allows all steps of the orthodontic treatment plan to be displayed without a separate virtual modeling file for each treatment step. Additionally, the processing circuitry can be configured to download a first treatment step of the virtual modeling file format, receive gingiva and teeth geometries corresponding to the first treatment step, and display the first treatment step. Further, a selected treatment step can be displayed based on information encoded into the orthodontic virtual modeling file format.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

An advantage of the orthodontics virtual modeling file format can be more precisely determining where the teeth will be over time without requiring extra storage space for individual files of each treatment step. Previously, a stand-alone 3D image had to be displayed when viewing a predetermined treatment step. The improved virtual modeling file format, however, is much more flexible and can step through time in smaller intervals without requiring any stand-alone 3D images to have been previously created and then displayed.

Rather than creating several stand-alone 3D images, the orthodontics virtual modeling file format can store original tooth shape and position as well as movement data for the teeth, thereby allowing the virtually modeled image to be adaptively displayed by calculating tooth position in real-time using transformation matrices. The position of each tooth can quickly and easily be determined relative to the original tooth position using the transformation matrices. Because the transformation matrices are encoded in the virtual modeling file format, the treatment step can be displayed using information from the virtual modeling file without having to create an additional virtual modeling file for displaying the selected treatment step.

The virtual modeling file format can also store key gingiva information to render the gingiva realistically rather than just filling a gap made by a tooth being moved.

Another advantage can be to host the virtual modeling file directly on a webpage (e.g., WebGL for 3D). A single virtual modeling file to display an entire treatment plan can minimize download and rendering time because after downloaded, the rest of the image can be quickly rendered with the information encoded into the virtual modeling file format. In other words, a lag time of rendering additional treatments steps has been removed. Previously, each of the treatment steps corresponding to two weeks, four weeks, six weeks, etc. were an independent or separate file that could require a significant amount of storage space (e.g., 2 megabytes each) which can quickly add up to a large file when showing a full treatment plan.

The virtual modeling file format includes a log of movement data that can determine how to move the patient's teeth when rendering it on the doctor's computer, for example, which results in less data needing to be stored compared to an individual file to display a 3D image for each treatment step. For example, if a tooth was rotated counter-clockwise by 2 degrees and that represents the new location of the tooth, that information can be stored in the virtual modeling file format and accessed when needing to display it rather than having a separate 3D file for each treatment step that contains all the positions of the teeth in each file. Once the movement data is provided, the software can move each tooth to where it should be based on a selected treatment step from the orthodontic treatment plan.

Additionally, when a tooth is moved, the gingiva is also affected. The gingiva can be redrawn so that they look correct and realistic. If a tooth is moved and nothing is done with the gingiva then there may be a big gap. For example, if the tooth has been moved back a millimeter then there is a millimeter groove in between the gingiva line and the tooth. The gingiva can then be redrawn by approximating where the gingiva would be based on the current gingiva location using its existing data. The amount of data required to redraw the gingiva entirely can be a significant amount of data which can be stored on a server or in a database, for example. Not all of the gingiva data can be stored in the virtual modeling file format because all of the data can't be transmitted efficiently and/or quickly. Included in the virtual modeling file downloaded on the doctor's computer can be key pieces of information corresponding to information about the gingiva. Once downloaded, JavaScript can be run locally on a computer, for example, to estimate where the gingiva should be. All the gingiva data could be up to 50 to 100 megabytes, for example, which would have to be downloaded. However, because only key pieces of information are delivered, the simulation can easily be run on the doctor's computer. Therefore, faster download and virtual model rendering on the doctor's station results in cheap computer power and can be faster because it's done locally on the doctor's computer. The gingiva data received from the server can be limited to strategically selected information, rather than receiving all the information corresponding to exactly what the gingiva would look like because that may be too much data to download efficiently and quickly. For example, strategically predetermined gingiva information (e.g., curve of the gingiva) can be accessed from the server and the software can fill in the gaps in information to draw the new gingiva. The gingiva drawing algorithm does not simply fill in the groove remaining from a moved tooth. Alternatively, the position of the current gingiva is understood and is used to provide an intelligent prediction of where the gingiva may be after the tooth is moved.

Figure 1:
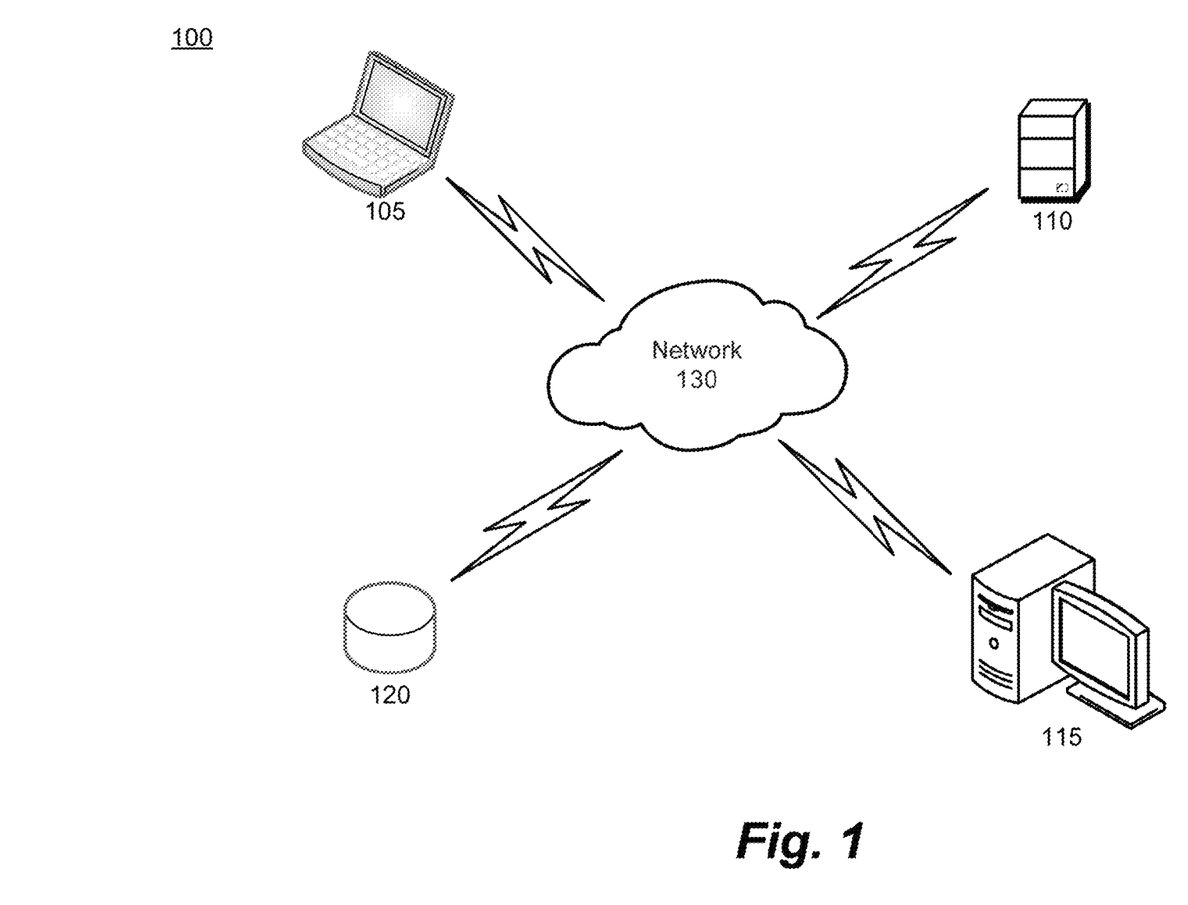
FIG. 1 depicts an exemplary network topology of a system for an orthodontics virtual modeling file format according to one or more embodiments of the disclosed subject matter.

Referring now to the drawings, wherein like reference numerals designate identical or corresponding parts throughout the several views, FIG. 1 depicts an orthodontics virtual modeling system (herein referred to as system 100) according to one or more embodiments of the disclosed subject matter. The system 100 can include a computer 115 connected to a mobile device 105, a server 110, and a database 120 via a network 130. The mobile device 105 can include a smart phone, a laptop, a PDA, a tablet, and the like. The mobile device 105 can represent one or more mobile devices connected to the server 110, the computer 115, and the database 120 via the network 130. The server 110 can represent one or more servers connected to the mobile device 105, the computer 115, and the database 120 via the network 130. The computer 115 can represent one or more computers connected to the mobile device 105, the server 110, and the database 120 via the network 130. The database 120 can represent one or more databases connected to the mobile device 105, the server 110, and the computer 115 via the network 130. The network 130 can represent one or more networks connecting the mobile device 105, the server 110, the computer 115, and the database 120.

The network 130 can be a public network, such as the Internet, or a private network such as a LAN or WAN network, or any combination thereof and can also include PSTN or ISDN sub-networks. The network 130 can also be wired, such as an Ethernet network, or can be wireless such as a cellular network including EDGE, 3G and 4G wireless cellular systems. The wireless network can also be Wi-Fi, Bluetooth, or any other wireless form of communication that is known.

The computer 115 can include an interface, such as a keyboard and/or mouse, allowing a user to interact with treatment steps corresponding to positions of a patient's teeth, for example, throughout a predetermined amount of time in which the patient's teeth move from a starting position to an ending position, for example. The position and movement of the patient's teeth can be virtually modeled (e.g., modeled in 3D) and displayed via the interface of the computer 115 via WebGL, for example.

The database 120 can store various information including patient data and corresponding virtual modeling files. The virtual modeling files can be encoded in a virtual modeling file format to store tooth shape, tooth position, tooth movement data, predetermined strategic gingiva information, and the like as further described herein. The gingiva information can be stored in the database 120. The database 120 can be local to the mobile device 105, the server 110, or the computer 115. Additionally, the database 120 can be an external database.

In one aspect, the server 110 can receive signals from the computer 115 and/or the mobile device 105 to cause the server 110 to transmit requested information (e.g., gingiva information such that a patient's gingiva can be rendered realistically after teeth movement) from the server 110 and/or database 120 to the computer 115 and/or mobile device 105. In another aspect, the server 110 can be a device that houses a processor including a computer (e.g., the computer 115), a laptop or smart phone (e.g., the mobile device 105), and the like such that the processing can be done locally.

Figure 2:
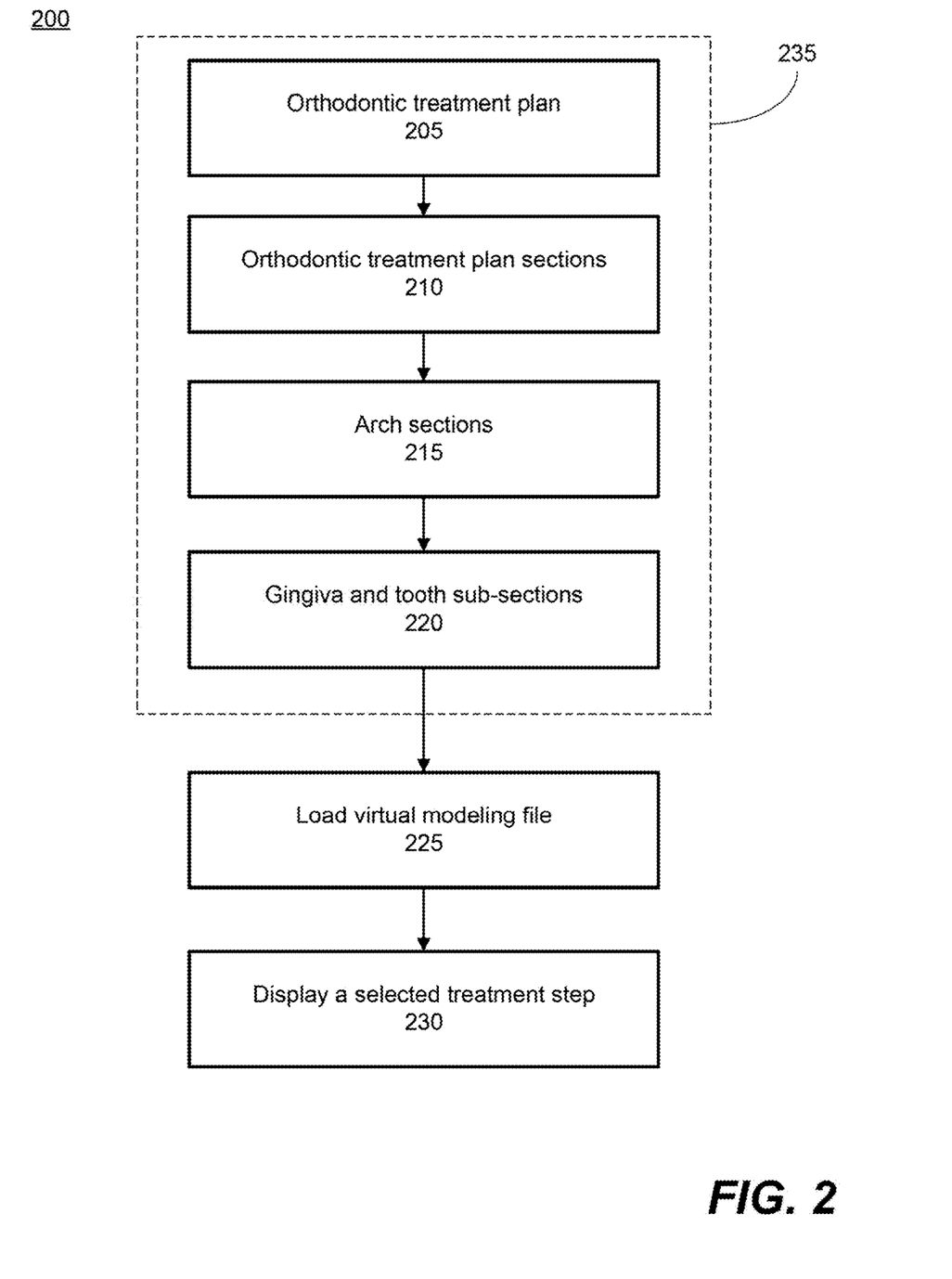
FIG. 2 depicts an orthodontics virtual modeling file format workflow according to one or more aspects of the disclosed subject matter.

FIG. 2 depicts an exemplary workflow according to one or more aspects of the invention. The work flow can include an encoding section 235, load the virtual modeling file 225, and display a treatment step 230. The encoding section 235 can include steps to develop an orthodontic treatment plan 205, divide the orthodontic treatment plan into sections 210 for each step of the treatment, each treatment step can be divided into arch sections 215 including a maxillary arch section and a mandibular arch section, and each arch can include gingiva and tooth sub-sections 220.

In section 205, the 3D file format includes a treatment plan for orthodontic treatment for an individual patient from the beginning of the treatment through the end of the treatment. As the treatment plan can be divided into sections 210 for each step of the treatment, each section can correspond to a time-step. For example, the first section (or time-step) can be equivalent to time zero, as in no treatment has been given, which can correspond to the original arch, teeth, and gingiva positions and shapes. Then the second, third, and fourth section can correspond to two weeks, four weeks, and six weeks, respectively. The time-step for each section can correspond to any amount of time based on the treatment plan, and the number of sections can be any number of sections based on the treatment plan.

In arch section 215 of the workflow, each treatment step can be divided into two sections of a maxillary arch section and a mandibular arch section. The maxillary arch and the mandibular arch are the arches formed by the teeth of the maxilla and the mandible, respectively. The maxillary arch section includes transformation information that can be used to align the maxillary arch on top of the mandibular arch. Additionally, for gingiva and tooth sub-sections 220, the maxillary arch section and the mandibular arch section includes sub-sections for the gingiva and for each tooth in the corresponding arch.

Next, loading the virtual modeling file in 225 can include reading the virtual modeling file to receive the encoded information of the virtual modeling file format. During the load operation, the information corresponding to the first section of the treatment plan (i.e., original shape and position of gingiva and teeth) is downloaded, the virtual modeling geometry information for the gingiva and teeth of each arch is read from the first section and loaded into memory (e.g., database 120 and/or local memory) of one or more of the mobile device 105, the server 110, and the computer 115.

The display a treatment step 230 includes displaying the gingiva and teeth in a shape and position corresponding to the selected treatment step. Before displaying the virtually modeled shapes of teeth, transformation matrices are passed to a renderer (e.g., WebGL for 3D rendering) and geometries of each tooth are displayed after transformation. The transformation of the gingiva can be manually applied to the gingiva geometry on affected vertices of the gingiva using transformation vectors loaded from the virtual modeling file. The updated gingiva geometry can be passed to the virtual modeling renderer for display. When the first treatment step is selected for display, no transformation will be applied to the teeth or gingiva and the original non-transformed geometries can be rendered. Additionally, when another treatment step is selected for display, transformation information of the previously loaded steps may be cached and kept in memory, if memory space allows, for faster transition between when selecting those previously selected and displayed treatment steps.

Figure 3:
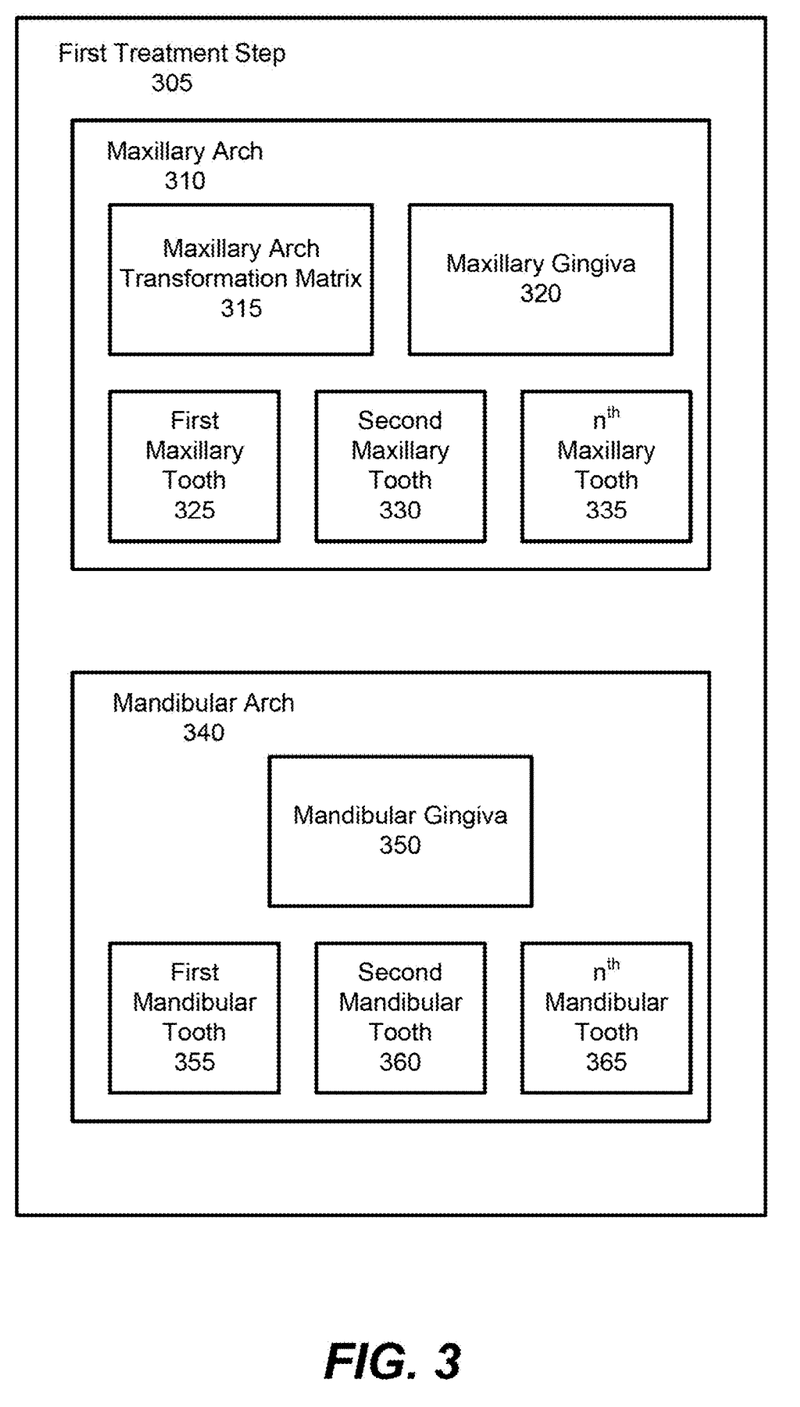
FIG. 3 depicts a block diagram of the information encoded in the virtual modeling file format for a first treatment step according to one or more embodiments of the disclosed subject matter.

FIG. 3 depicts a block diagram of the information encoded in the virtual modeling file format for a first treatment step 305 according to one or more embodiments of the disclosed subject matter. The virtual modeling file format includes each step of the orthodontic treatment plan. In one aspect, the first treatment step 305 can include a maxillary arch 310 and a mandibular arch 340. The maxillary arch 310 can include a maxillary arch transformation matrix 315, maxillary gingiva 320, a first maxillary tooth 325, a second maxillary tooth 330, and an $n^{th}$ maxillary tooth 335 where the $n^{th}$ maxillary tooth 335 represents a predetermined number of teeth and corresponding data within the maxillary arch 310 based on the patient. The maxillary arch transformation matrix 315 can be used to align the maxillary arch 310 on top of a mandibular arch 340 when displayed.

In the first treatment step 305, the maxillary gingiva 320 can include geometry information, where geometry information can be the shape of the maxillary gingiva 320. Transformation information is not needed in the first treatment step 305 because the first treatment step 305 can correspond to the original shape and position of the gingiva and each tooth in the maxillary arch. The first maxillary tooth 325, the second maxillary tooth 330, and all other maxillary teeth associated with the maxillary arch 310 include geometry information, where geometry information of the maxillary teeth can be shape and position. The maxillary gingiva 320 and maxillary teeth do not need transformation information for the first treatment step 305 because the maxillary teeth in the first treatment step 305 can be displayed in their original shape and position.

The mandibular arch 340 can include a mandibular gingiva 350, a first mandibular tooth 355, a second mandibular tooth 360, and an $n^{th}$ mandibular tooth 365 where the $n^{th}$ mandibular tooth 365 represents a predetermined number of teeth and corresponding data within the mandibular arch 340 based on the patient.

In the first treatment step 305, the mandibular gingiva 350 can include geometry information where the geometry information can be the shape of the mandibular gingiva 350. The first mandibular tooth 355, the second mandibular tooth 360, and all other mandibular teeth associated with the mandibular arch 340 include geometry information, where geometry information of the mandibular teeth can be shape and position. The mandibular gingiva 350 and mandibular teeth do not need transformation information for the first treatment step 305 because the mandibular teeth in the first treatment step 305 can be displayed in their original shape and position.

Figure 4:
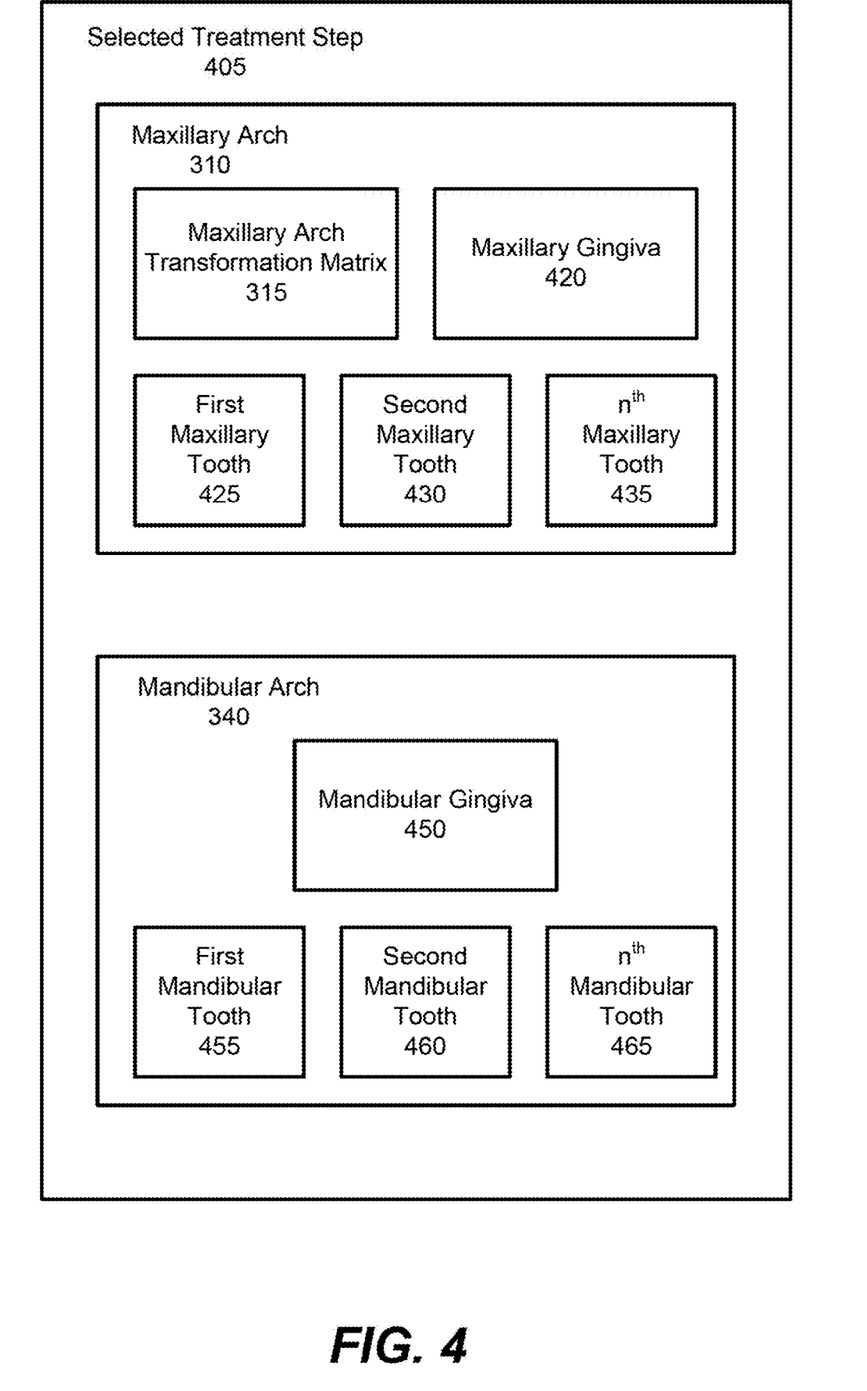
FIG. 4 depicts a block diagram of the information encoded in the virtual modeling file format for a selected treatment step according to one or more embodiments of the disclosed subject matter.

FIG. 4 depicts a block diagram of the information encoded in the virtual modeling file format for a selected treatment step 405 according to one or more embodiments of the disclosed subject matter. The selected treatment step 405 can represent each treatment step of the treatment plan other than the first treatment step 305. As the selected step 405 can be part of the same treatment plan for a patient, the maxillary arch 310 and the mandibular arch 340 can be included in the selected treatment step 405 and can be the same arches used in the first treatment step 305. The maxillary arch 310 can include the maxillary arch transformation matrix 315 which can be the same maxillary arch transformation matrix 315 from the first treatment step 305 because the treatment plan is for the same patient. Additionally, the maxillary arch 310 can include maxillary gingiva 420, a first maxillary tooth 425, a second maxillary tooth 430, and an $n^{th}$ maxillary tooth 435 where the $n^{th}$ maxillary tooth 435 represents a predetermined number of teeth and corresponding data within the maxillary arch 310 based on the patient. The maxillary arch transformation matrix 315 can be used to align the maxillary arch 310 on top of the mandibular arch 340 when displayed.

In the selected treatment step 405, the maxillary gingiva 420 can include transformation vectors, where the transformation vectors can be a list of 3D vectors, for example, to determine the shape of the maxillary gingiva 420 such that the number of 3D vectors is proportional to the number of vertices in the gingiva. The first maxillary tooth 425, the second maxillary tooth 430, and any other maxillary teeth associated with the maxillary arch 310 in the selected treatment step 405 can include a transformation matrix which defines the movement of the teeth in each selected treatment step 405 using a 4×4 matrix of 16-bit float numbers.

The mandibular arch 340 can include a mandibular gingiva 450, a first mandibular tooth 455, a second mandibular tooth 460, and an $n^{th}$ mandibular tooth 365 where the $n^{th}$ mandibular tooth 365 represents a predetermined number of teeth and corresponding data within the mandibular arch 340 based on the patient.

In the selected treatment step 405, the mandibular gingiva 450 can include transformation vectors, where the transformation vectors can be a list of 3D vectors, for example, to determine the shape of the mandibular gingiva 450 such that the number of 3D vectors is proportional to the number of vertices in the gingiva. The first mandibular tooth 455, the second mandibular tooth 460, and all other mandibular teeth associated with the mandibular arch 340 in the selected treatment step 405 can include a transformation matrix which defines the movement of the teeth in each selected treatment step 405 using a 4×4 matrix of 16-bit float numbers.

Figure 5:
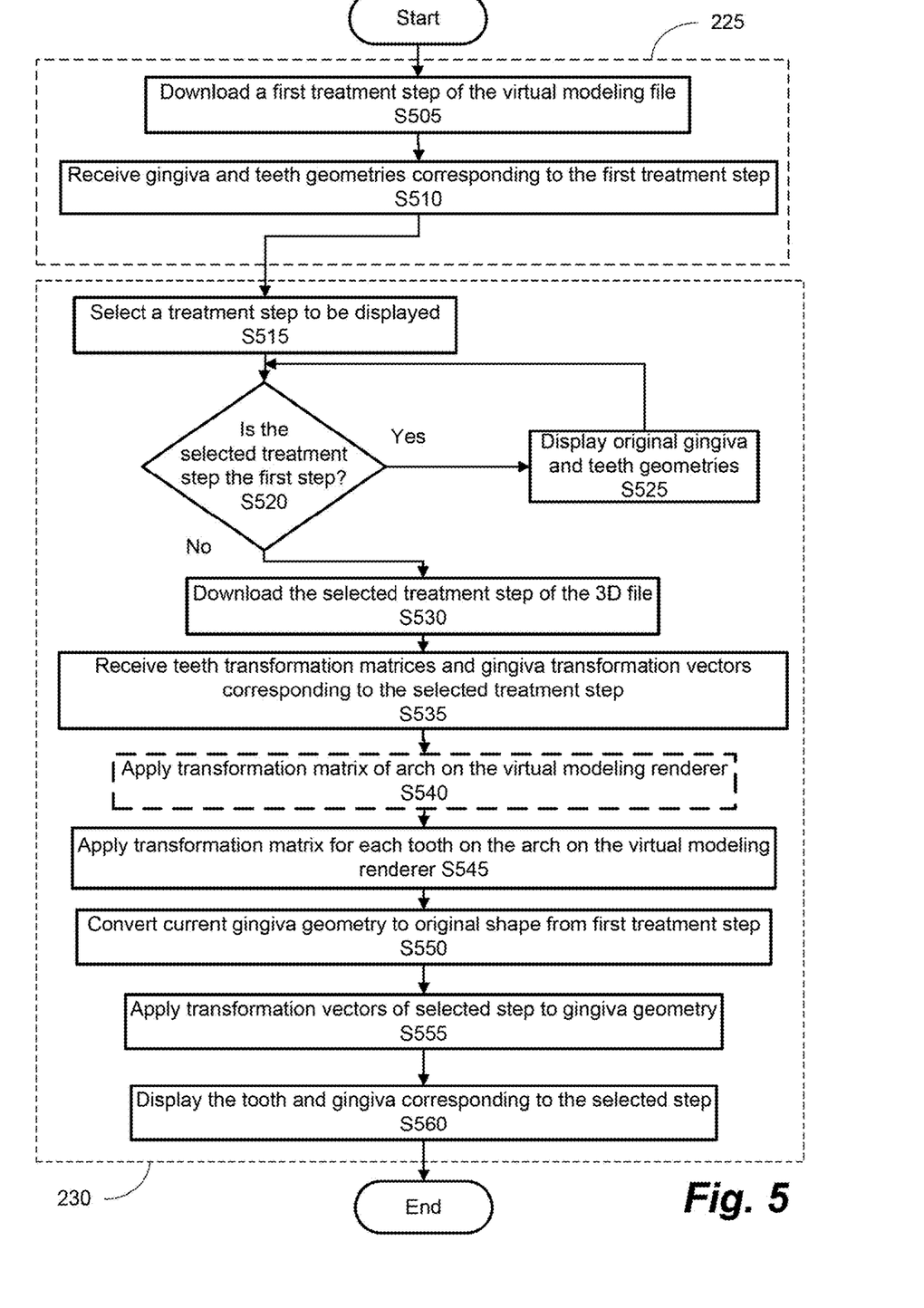
FIG. 5 is an algorithmic flow chart of displaying an orthodontic treatment plan using an orthodontic virtual modeling file format according to one or more embodiments of the disclosed subject matter.

FIG. 5 is an algorithmic flow chart of displaying an orthodontic treatment plan using an orthodontic virtual modeling file format according to one or more embodiments of the disclosed subject matter.

In S505, a first treatment step of the virtual modeling file can be downloaded. The first treatment step downloaded in S505 can include the information corresponding to the first treatment step encoded in the virtual modeling file as depicted in FIG. 3.

In S510, the gingiva and teeth geometries corresponding to the first treatment step 305 can be received. S505 and S510 can be included in the load virtual modeling file 225 section of the workflow in FIG. 2.

In S515, a treatment step can be selected for display.

In S520, it can be determined if the selected treatment step for display from S515 is the first treatment step 305. If the selected treatment step 405 from S515 is not the first treatment step 305, then the selected treatment step 405 of the virtual modeling file can be downloaded in S530. However, if the requested treatment step from S515 is the first treatment step 305, then the original gingiva and teeth geometries can be displayed in S525.

In S525, displaying the original gingiva and teeth geometries can include displaying the original gingiva and teeth geometries of the mandibular arch 340, applying the maxillary arch transformation matrix 315, and displaying the original gingiva and teeth geometries of the maxillary arch 340. Once the original gingiva and teeth geometries have been displayed in S525, the process can return to S520 to determine if the selected treatment step 405 is the first treatment step 305.

In S530, the selected treatment step 405 of the virtual modeling file can be downloaded.

In S535, teeth transformation matrices and gingiva transformation vectors corresponding to the selected treatment step 405 can be received.

In S540, a transformation matrix of an arch can be applied on a virtual modeling renderer. S540 can be optional as the transformation matrix (i.e., maxillary arch transformation matrix) of the arch is only applied when the arch is the maxillary arch 310.

In S545, a transformation matrix for each tooth on the corresponding arch can be applied on the virtual modeling renderer.

In S550, current gingiva geometry of the selected treatment step 405 can be converted to the original gingiva shape of the first treatment step 305.

In S555, transformation vectors of the selected step 405 can be applied to the gingiva geometry of the first treatment step 305.

In S560, the tooth and gingiva corresponding to the selected treatment step 405 based on the movement of each tooth and shape of the gingiva from the transformation matrices and transformation vectors, respectively, can be displayed as a virtually modeled figure, such as a 3D virtual model, for example.

S515 through S560 can be included in the display a selected treatment step 230 from the workflow depicted in FIG. 2.

It should be noted that the steps discussed above with respect to FIG. 5 do not have to be performed in that particular order. Various steps could be reversed, performed independently, performed in various orders, or performed simultaneously.

Figure 6:
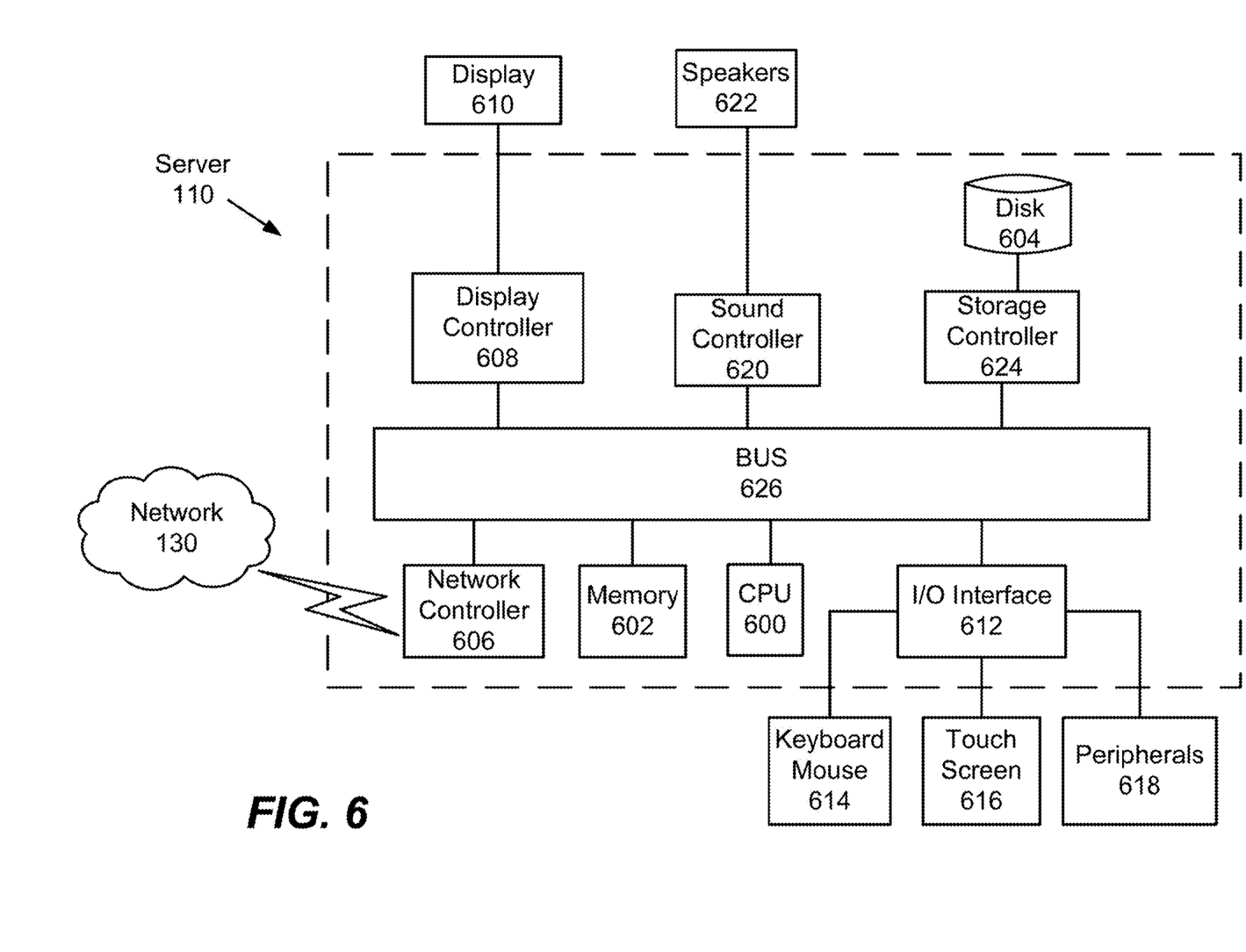
FIG. 6 is a hardware block diagram of a server according to one or more exemplary aspects of the disclosed subject matter.

Next, a hardware description of the server 110 according to exemplary embodiments is described with reference to FIG. 6. In FIG. 6, the server 110 includes a CPU 600 which performs the processes described above/below. The process data and instructions may be stored in memory 602. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the server 110 communicates, such as a server or computer.

The functions and features described herein may also be executed by various distributed components of a system. For example, one or more processors may execute these system functions, wherein the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Having now described embodiments of the disclosed subject matter, it should be apparent to those skilled in the art that the foregoing is merely illustrative and not limiting, having been presented by way of example only. Thus, although particular configurations have been discussed herein, other configurations can also be employed. Numerous modifications and other embodiments (e.g., combinations, rearrangements, etc.) are enabled by the present disclosure and are within the scope of one of ordinary skill in the art and are contemplated as falling within the scope of the disclosed subject matter and any equivalents thereto. Features of the disclosed embodiments can be combined, rearranged, omitted, etc., within the scope of the invention to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the disclosed subject matter.

The invention claimed is:

1. An orthodontics virtual modeling system for modeling teeth of a patient, comprising:
   a server including processing circuitry configured to
      receive a virtual modeling file including an orthodontic treatment plan such that the virtual modeling file provides for display of all of a plurality of treatment steps of the orthodontic treatment plan to be displayed;

receive one or more data sections of a first treatment step of the plurality of treatment steps of the virtual modeling file;
access gingiva geometries and teeth geometries from the one or more data sections of the first treatment step;
receive one or more data sections of an interim treatment step of the plurality of treatment steps of the virtual modeling file, wherein the interim treatment step is different than the first treatment step;
access teeth transformation matrices and a plurality of gingiva transformation vectors for the interim treatment step from the one or more data sections of the interim treatment step, wherein
the one or more data sections for each of the plurality of treatment steps include a respective plurality of gingiva transformation vectors, and
the plurality of gingiva transformation vectors include a set of 3D vectors defining a shape of the respective gingiva according to the interim treatment step, wherein
a number of vectors in the set of 3D vectors is proportional to a number of vertices in the gingiva geometries;
apply the teeth transformation matrices to the teeth geometries to obtain interim teeth geometries corresponding to the interim treatment step;
apply the gingiva transformation vectors to the gingiva geometries to obtain interim gingiva geometries corresponding to the interim treatment step; and
display the interim treatment step based on rendering the interim gingiva geometries and the interim teeth geometries.

2. The orthodontics virtual modeling system of claim 1, wherein each treatment step of the plurality of treatment steps in the virtual modeling file comprises a maxillary arch data section and a mandibular arch data section.

3. The orthodontics virtual modeling system of claim 2, wherein the maxillary arch data section and the mandibular arch data section each comprise a respective geometry for each tooth of the teeth and a respective plurality of transformation vectors for each tooth of the teeth.

4. The orthodontics virtual modeling system of claim 3, wherein the respective geometry for each tooth of the teeth comprises a shape and a position for the respective tooth.

5. The orthodontics virtual modeling system of claim 2, wherein the maxillary arch data section comprises a maxillary arch transformation matrix for aligning a maxillary arch with a mandibular arch of the patient.

6. The orthodontics virtual modeling system of claim 5, wherein the processing circuitry is further configured to:
determine that the interim treatment step corresponds to the maxillary arch; and
apply the maxillary arch transformation matrix on a 3D modeling renderer.

7. The orthodontics virtual modeling system of claim 6, wherein the maxillary arch transformation matrix for defining movement of the teeth in the interim treatment step is a 4×4 matrix.

8. A method of displaying an orthodontic treatment plan for treating teeth of a patient from an orthodontic virtual modeling file format, comprising:
receiving, via processing circuitry, a virtual modeling file including an orthodontic treatment plan such that the virtual modeling file provides for display of all of a plurality of treatment steps of the orthodontic treatment plan;
receiving, via the processing circuitry, one or more data sections of a first treatment step of the plurality of treatment steps of the virtual modeling file;
accessing, via the processing circuitry, gingiva geometries and teeth geometries from the one or more data sections of the first treatment step;
receiving, via the processing circuitry, one or more data sections of an interim treatment step of the plurality of treatment steps of the virtual modeling file, wherein the interim treatment step is different than the first treatment step;
accessing, via the processing circuitry, teeth transformation matrices and a plurality of gingiva transformation vectors for the interim treatment step from the one or more data sections of the interim treatment step, wherein
the one or more data sections for each of the plurality of treatment steps include a respective plurality of gingiva transformation vectors, and
the plurality of gingiva transformation vectors include a set of 3D vectors defining a shape of the respective gingiva according to the interim treatment step, wherein
a number of vectors in the set of 3D vectors is proportional to a number of vertices in the gingiva geometries;
applying, via the processing circuitry, the teeth transformation matrices to the teeth geometries to obtain interim teeth geometries corresponding to the interim treatment step;
applying, via the processing circuitry, the gingiva transformation vectors to the gingiva geometries to obtain interim gingiva geometries corresponding to the interim treatment step; and
displaying, via the processing circuitry, the interim treatment step based on rendering the interim gingiva geometries and the interim teeth geometries.

9. The method of claim 8, wherein each step of the plurality of treatment steps in the virtual modeling file includes a maxillary arch data section and a mandibular arch data section.

10. The method of claim 9, wherein the maxillary arch data section and the mandibular arch data section each comprise a respective geometry for each tooth of the teeth and a respective plurality of transformation vectors for each tooth of the teeth.

11. The method of claim 10, wherein the respective geometry for each tooth of the teeth comprises a shape and a position for the respective tooth.

12. The method of claim 9, wherein the maxillary arch data section comprises a maxillary arch transformation matrix for aligning a maxillary arch with a mandibular arch of the patient.

13. A non-transitory computer-readable storage medium storing computer-readable instructions that, when executed by a computer, cause the computer to perform a method of displaying an orthodontic treatment plan for treating teeth of a patient from an orthodontic virtual modeling file format, the method comprising:
providing a virtual modeling file including an orthodontic treatment plan such that encoded information of the virtual modeling file allows all of a plurality of treatment steps of the orthodontic treatment plan to be displayed;
uploading one or more data sections of a first treatment step of the plurality of treatment steps of the virtual modeling file, wherein the one or more data sections of the first treatment step include gingiva geometries and teeth geometries;

uploading one or more data sections of an interim treatment step of the plurality of treatment steps of the virtual modeling file,
  wherein the interim treatment step is different than the first treatment step, and
  wherein the one or more data sections of the interim treatment step include teeth transformation matrices and a plurality gingiva transformation vectors for the interim treatment step, wherein
    the one or more data sections for each of the plurality of treatment steps include a respective plurality of gingiva transformation vectors, and
    the plurality of gingiva transformation vectors include a set of 3D vectors defining a shape of the respective gingiva according to the interim treatment step, wherein
      a number of vectors in the set of 3D vectors is proportional to a number of vertices in the gingiva geometries; and viewing the interim treatment step via a virtual rendering of interim gingiva geometries and interim teeth geometries of the interim step, wherein
  the interim teeth geometries are generated through application of the teeth transformation matrices to the teeth geometries, and
  the interim gingiva geometries are generated through application of the gingiva transformation vectors to the gingiva geometries.

14. The non-transitory computer-readable storage medium of claim 13, wherein each treatment step of the plurality of treatment steps in the virtual modeling file includes a maxillary arch data section and a mandibular arch data section.

15. The non-transitory computer-readable storage medium of claim 14, wherein the maxillary arch data section and the mandibular arch data section each comprise a respective geometry for each tooth of the teeth and a respective plurality of transformation vectors for each tooth of the teeth.

16. The non-transitory computer-readable storage medium of claim 15, wherein the respective geometry for each tooth of the teeth comprises a shape and a position for the respective tooth.

17. The non-transitory computer-readable storage medium of claim 14, wherein the maxillary arch data section comprises a maxillary arch transformation matrix for aligning a maxillary arch with a mandibular arch of the patient.

* * * * *